United States Patent
Jan et al.

(10) Patent No.: US 7,778,452 B2
(45) Date of Patent: Aug. 17, 2010

(54) IMAGE RECONSTRUCTION METHOD FOR STRUCTURING TWO-DIMENSIONAL PLANAR IMAGING INTO THREE-DIMENSION IMAGING

(75) Inventors: Meei-Ling Jan, Taoyuan County (TW); Keh-Shih Chiang, Hsinchu (TW); Yu-Ching Ni, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 909 days.

(21) Appl. No.: 11/562,878

(22) Filed: Nov. 22, 2006

(65) Prior Publication Data
US 2007/0242867 A1    Oct. 18, 2007

(30) Foreign Application Priority Data
Apr. 18, 2006    (TW) ............................. 95113726 A

(51) Int. Cl.
*G06K 9/00*    (2006.01)
*G01T 1/164*    (2006.01)
*G01T 1/166*    (2006.01)
*A61B 6/00*    (2006.01)

(52) U.S. Cl. ..................... 382/128; 382/100; 382/131; 250/363.03; 250/363.04; 600/436; 378/4

(58) Field of Classification Search ................ 382/100, 382/128, 131, 154; 250/363.03, 363.04, 250/369, 362; 378/4, 21, 901, 62; 600/436
See application file for complete search history.

(56) References Cited

U.S. PATENT DOCUMENTS

| | | | |
|---|---|---|---|
| 5,224,037 A * | 6/1993 | Jones et al. | ............... 382/131 |
| 5,793,045 A | 8/1998 | DiFilippo et al. | |
| 6,804,325 B1 | 10/2004 | Smith | |

(Continued)

OTHER PUBLICATIONS

Meei-Ling Jan, Development of Non-invasive Imaging Systems and a 3D Automatic Registration Method for Molecular Imaging Applications, Doctoral thesis from National Tsing Hua University, Jun. 2005, pp. 1-4. Taiwan.

*Primary Examiner*—Sheela C Chawan
(74) *Attorney, Agent, or Firm*—WPAT, PC; Justin King

(57) ABSTRACT

An image reconstruction method for structuring planar images into three-dimension images is disclosed in the present invention. The image reconstruction method, being adopted to perform an image reconstruction operation upon a measured value of at least a line of response (LOR) obtained by detecting an object-to-be-imaged using an inspection system, comprises steps of: utilizing a plurality of voxels, each having a first radioactivity value, to construct an image domain with reference to the object-to-be-imaged; projecting the LOR while comparing the result of the projection with the measured value to obtain a calibrated value; performing a back-projection operation basing on the relationship between the calibrated value and the first radioactivity value of each voxel of the LOR; performing a calculation basing on the relationship between the calibrated value and the first radioactivity value of each voxel to obtain a second radioactivity value; utilizing the second radioactivity value to update the first radioactivity value of each voxel of the LOR while enabling an image reconstruction operation by an iteration manner. By the method of the invention, images with preferred contrast comparing to those of prior art can be obtained such that the method of the invention can have better tumor detection ability.

6 Claims, 11 Drawing Sheets

22

- 220: performing a calculation upon the first radioactivity value of each voxel of each LOR with respect to the calibrated value of its corresponding LOR so as to obtain a weighting for each voxel

- 221: back-projecting each voxel of each LOR back to the image domain basing on the weighting of each voxel

U.S. PATENT DOCUMENTS

| | | | |
|---|---|---|---|
| 7,227,149 B2 * | 6/2007 | Stearns et al. | 250/363.03 |
| 7,405,405 B2 * | 7/2008 | Stearns et al. | 250/363.03 |
| 7,599,540 B2 * | 10/2009 | Koehler | 382/130 |

* cited by examiner

21 projecting the first radioactivity values of voxels selected form the plural voxels to a projection domain with respect to one of the plural LORs passing the selected voxel so as to correspondingly obtain an projection value for each LOR — 210 summing up the projection values of the voxels passing by the same LOR for obtaining an estimated projection value of each LOR — 211 comparing the estimated projection value to the measured value of each LOR so as to obtain a calibrated value for each LOR — 212

IMAGE RECONSTRUCTION METHOD FOR STRUCTURING TWO-DIMENSIONAL PLANAR IMAGING INTO THREE-DIMENSION IMAGING

FIELD OF THE INVENTION

The present invention relates to an image reconstruction method, and more particularly, to an image reconstruction method employing an iterative back-projection means to reconstruct weighting of projection data so as to achieve three-dimensional imaging with improved contrast.

BACKGROUND OF THE INVENTION

Cancer is a state of cellular growth occurring when some normal cells become abnormal and continue to grow abnormally, which, in the many forms we know it, is a disease of civilization, and is practically unknown among primitive people properly nourished on a simple natural diet and lived by a simply lifestyle. Nowadays, cancer is becoming the major cause of deaths in many parts of the world. Early detection has been demonstrated to be the most effective strategy to reduce cancer mortality. Thanks to the development of modern technology, a plurality of non-invasive diagnostic examination devices, that involve the acquisition of physiologic images based on the detection of molecular biological processes, have been developed and thus the probability of early detection has been greatly increased. Among those diagnostic examination devices, the usefulness of positron emission tomography (PET) imaging has recently become accepted, not only in research, but also in clinical fields.

PET is a nuclear medicine medical imaging technique which produces a three dimensional image in the body, in which a short-lived radioactive tracer isotope which decays by emitting a positron ($\beta^+$), chemically incorporated into a metabolically active molecule, such as glucose or amino-acid, etc., is injected into the blood circulation of a living subject by intravenous injection. There is a waiting period while the metabolically active molecule becomes concentrated in tissues of interest, then the subject is placed in the imaging scanner. The short-lived isotope decays, emitting a positron. After travelling up to a few millimeters, the positron annihilates with an electron, producing a pair of annihilation photons, which is similar to gamma ($\gamma$) rays of 511 keV moving in opposite directions, i.e. being emitted 180° apart. These are detected when they reach a scintillator material in the scanning device, creating a burst of light which is detected by photomultiplier tubes where it is converted and amplifuied into digital signals. The technique depends on simultaneous or coincident detection of the pair of photons. The digital signals are reconstructed by processes of binning, rebinning and image-reconstructing so as to plot a map of the distribution of the gamma rays.

As a conventional image reconstruction method shown in FIG. 1 where we have an annihilation referred as an event, the gamma ray is traveling at opposite directions and detected in detectors and a line of response (LOR) 12 is drawn in between those two detectors 10, 11, moreover, associated with that line of response 12 are two paired scintillator crystals respectively arranged on the two detectors 10, 11. By which, as an annihilation event of the LOR 12 is detected by the two detectors 10, 11, the counting of the LOR 12 is increased by one. It is known that, during a specific scanning period, there may be a plurality of annihilation events relating to the LOR 12 as the counting thereof accumulated therewith, and the point of interaction or annihilation can be any point on the LOR 12.

However, the conventional image reconstruction method of FIG. 1 is based on an assumption that any positron annihilation is occurred right at the middle of its corresponding LOR and can be determined at the intersection of the focal place, such as the A, B and C planes of FIG. 1, with the LOR.

The abovementioned focal place tomography is disclosed by H. Uchida et al, in "A compact planar positron imaging system," Nucl. Instrum. Methods Phys Res. A, vol. 516, pp. 564-574, 2004. The focal place tomography can only reconstruct a planar image with respect to the coordinate (X, Y) data on a focal plane, but the data of an annihilation relating the a third dimension represented by the Z direction of FIG. 1 is missed. In addition, a nuclear imaging using variable weighting is disclosed in U.S. Pat. No. 5,793,045, which use a weight processor to weight each coincidence event based on the energy of the detected gamma rays. For instance, a true event occurs when a gamma ray is detected without having been scattered. Not having been scattered, these gamma rays are characterized by energies in the region of the primary photopeak of the particular radiopharmaceutical in use (e.g. 511 keV for gamma rays generated by positron annihilation). Detected events in the upper portion of the primary photopeak are particularly unlikely to have been scattered. The positions of these events can therefore be determined with an especially high degree of confidence. As a result, true events contribute positively to image quality. Nevertheless, the image reconstruction method disclosed in U.S. Pat. No. 5,793,045 is still a planar image reconstruction method that it can not determine effectively the exact position of each annihilation. Moreover, the contrast of the image reconstructed thereby is poor while there are a plurality of positron annihilations in an object-to-be-detected.

In the conventional method disclosed in U.S. Pat. No. 6,804,325, entitled "Method for positron emission mammography image reconstruction", the image reconstruction is implemented either by backprojection image reconstruction or by iterative image reconstruction utilizing maximum likelihood expectation maximization (MLEM). However, in the backprojection image reconstruction provided in the forgoing U.S. patent, the probability of each positron annihilation is assumed to be the same.

Therefore, it is in need of an image reconstruction method for achieving three-dimensional imaging with improved contrast and better tumor-detection accuracy on an objected to be imaged, that it is cost-saving and can perform a scan with less time comparing to those of conventional planar imaging systems.

SUMMARY OF THE INVENTION

In view of the disadvantages of prior art, the primary object of the present invention is to provide an image reconstruction method employing an iterative back-projection means to reconstruct weighting of projection data so as to achieve three-dimensional imaging with improved contrast.

The primary object of the invention an image reconstruction method for structuring planar images into three-dimension images that can be implemented by a simplified imaging apparatus, and thus the cost of image reconstruction is reduced.

To achieve the above objects, the present invention provides an image reconstruction method for structuring planar images into three-dimension images, being adopted to perform an image reconstruction operation with respect to a plurality of measured values, respectively corresponding to a plurality of lines of response (LOR) obtained from the detecting of an object-to-be-imaged, which comprises steps of: (a)

utilizing a plurality of voxels, each having a first radioactivity value, to construct an image domain with reference to the object-to-be-imaged; (b) projecting the plural voxels with respect to each LOR in respective for converting the same to a projection domain while comparing the result of the projection respectively with the measured values to obtain a plurality of calibrated values corresponding to the plural LORs in respective; (c) obtaining a weighting for each voxel based on an operation performed upon the first radioactivity value of each voxel with respect to a corresponding LOR; (d) performing a back-projection operation basing on the weighting of each voxel of each LOR so as to perform a calculation upon the calibrated values of each LOR wit respect to the weightings for obtaining a second radioactivity value for each voxel of each LOR; (e) converting the second radioactivity value of each voxel into an updated first radioactivity value by projecting the same back to the image domain; and (f) repeating the step (b) to step (f) by an iterative manner.

Preferably, step (b) further comprises steps of: (b1) projecting the first radioactivity values of voxels selected form the plural voxels to a projection domain with respect to one of the plural LORs passing the selected voxel so as to correspondingly obtain an estimated projection value for each LOR; and (b2) comparing the estimated projection value to the measured value of each LOR so as to obtain a calibrated value for each LOR. It is noted that the calibrated value can be the ratio of the measured value and the estimated projection value.

Preferably, step (d) further comprises a steps of: (d1) defining a threshold value and setting the second radioactivity value to be zero while the second radioactivity value is smaller than the threshold value.

Preferably, the weighting of a voxel with respect to a LOR is the ratio of the first radioactivity value of the voxel and the totality of the first radioactivity value of all voxels passing by the LOR.

Preferably, the calculation of step (d) further comprises steps of: obtaining a product value by multiplying each weight of each voxel of each LOR by it corresponding calibrated value; summing up the product values of the same LOR to obtain the second radioactivity value for each voxel of each LOR; and defining a threshold value and setting the second radioactivity value to be zero while the second radioactivity value is smaller than the threshold value.

Other aspects and advantages of the present invention will become apparent from the following detailed description, taken in conjunction with the accompanying drawings, illustrating by way of example the principles of the present invention.

BRIEF DESCRIPTION OF THE DRAWINGS

FIG. 2B is a flow chart showing steps for generating the calibrated values according to a preferred embodiment of the invention.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as the follows.

Figure 1:
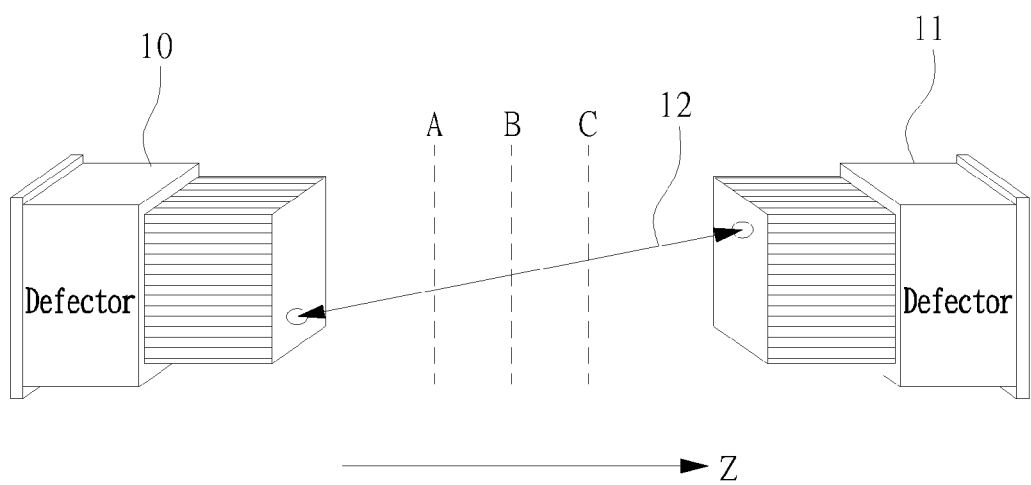
FIG. 1 is a schematic diagram depicting a conventional image reconstruction method.
Figure 2A:
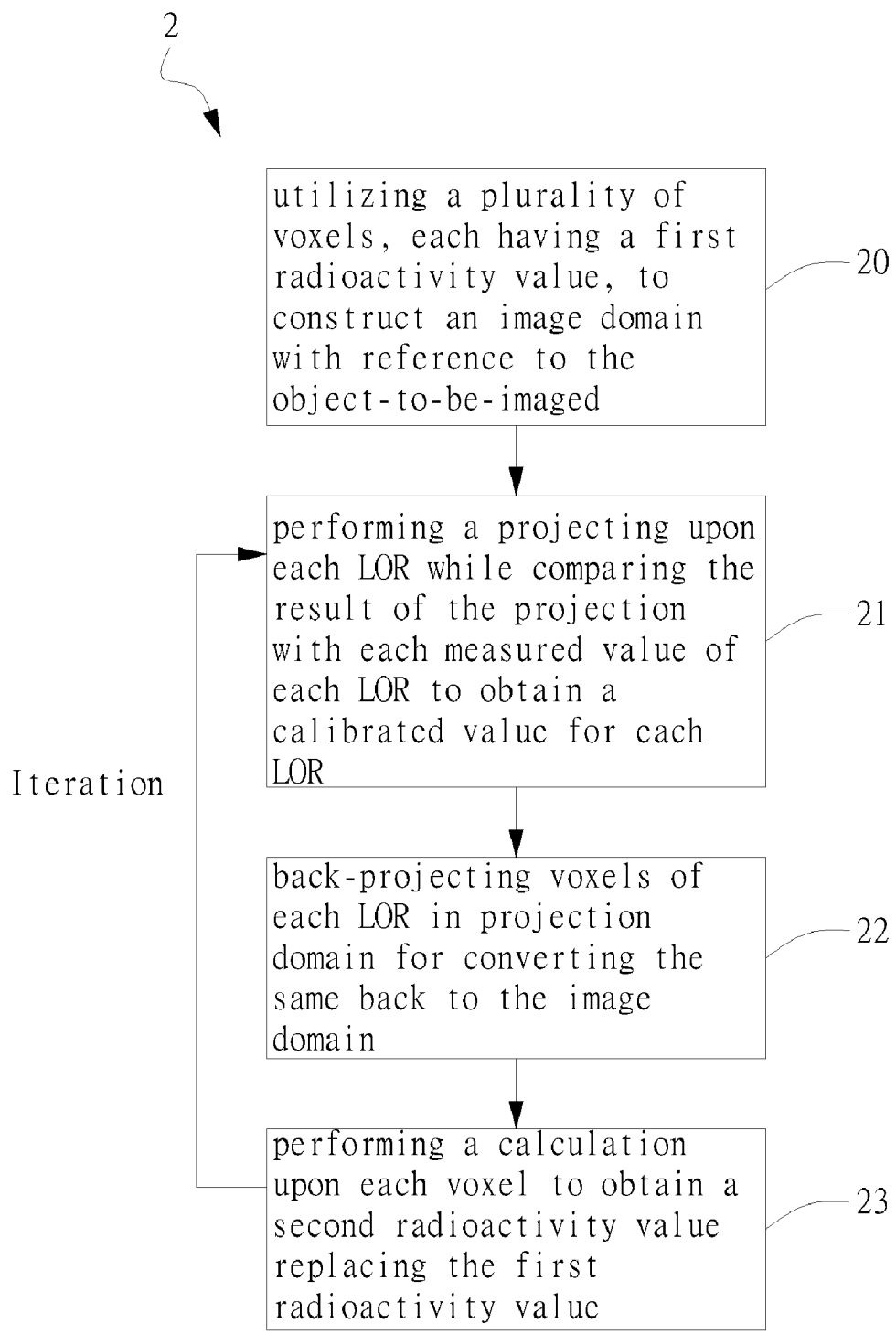
FIG. 2A is a flow chart illustrating an image reconstruction method according to a preferred embodiment of the invention.

Please refer to FIG. 2A, which is a flow chart illustrating an image reconstruction method according to a preferred embodiment of the invention. The image reconstruction method is adopted to perform an image reconstruction operation upon a measured value of at least a line of response (LOR) obtained by detecting an object-to-be-imaged using an inspection system, that processing flow of the image reconstruction method 2 of the invention starts from step 20: utilizing a plurality of voxels, each having a first radioactivity value, to construct an image domain with reference to the object-to-be-imaged.

Figure 2C:
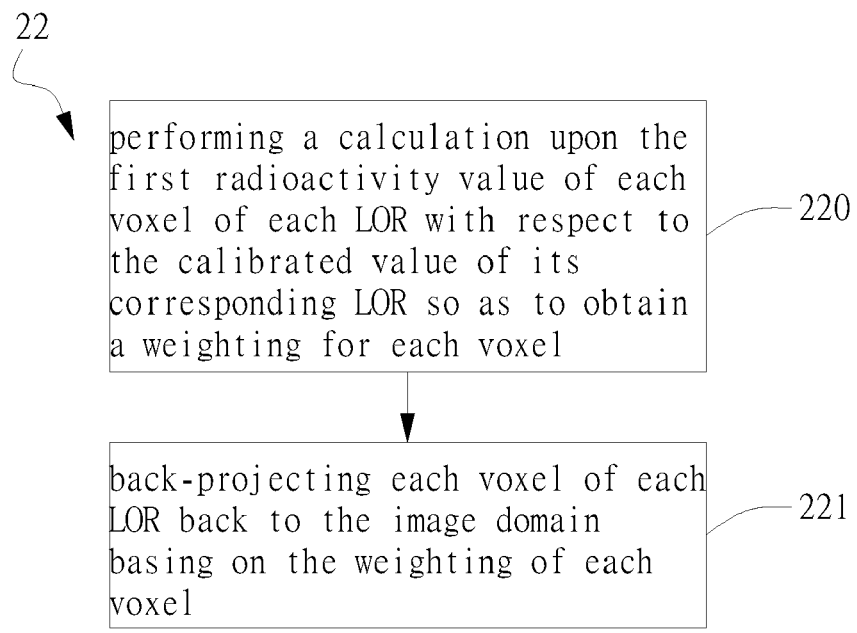
FIG. 2C is a flow chart showing steps for generating the weightings according to a preferred embodiment of the invention.
Figure 2D:
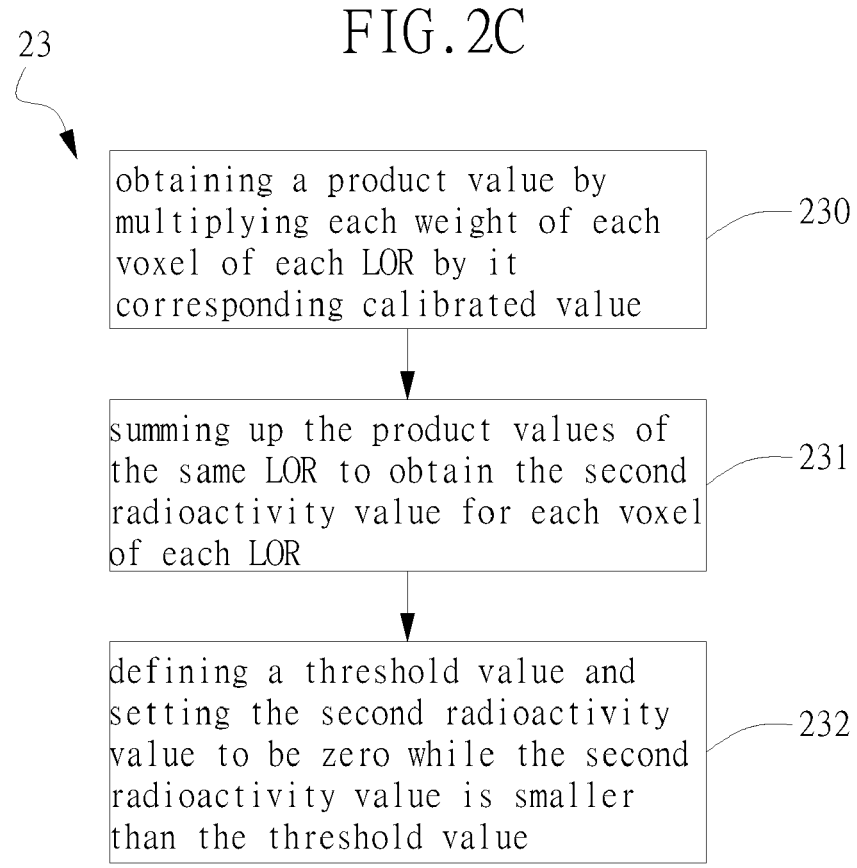
FIG. 2D is a flow chart showing steps for generating the second radioactivity values according to a preferred embodiment of the invention.
Figure 3A:
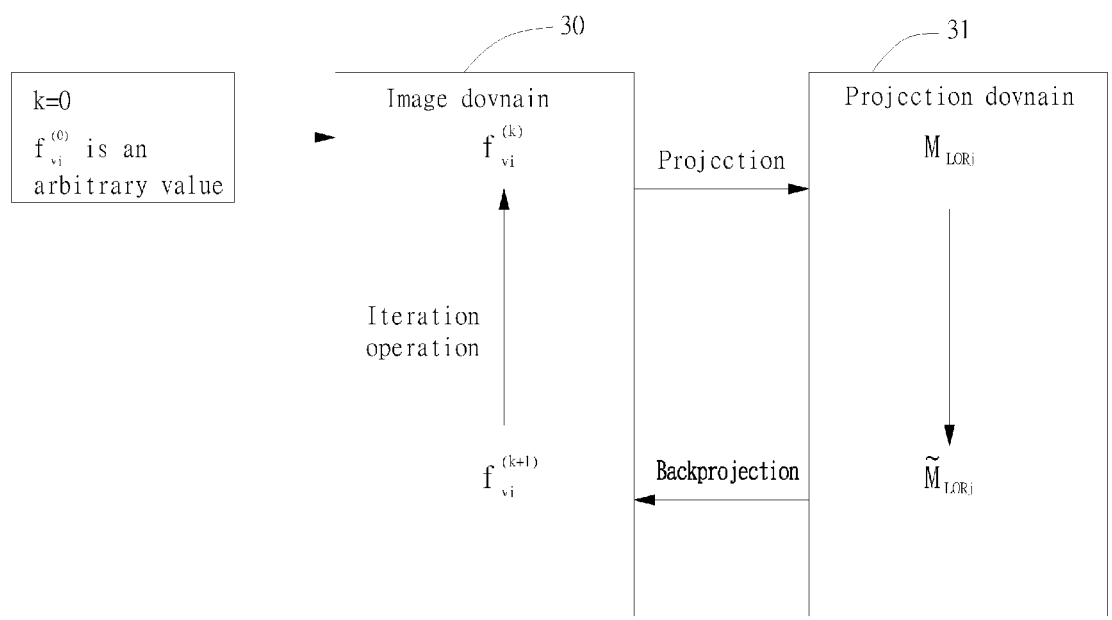
FIG. 3A is a block diagram depicting the concept of an image reconstruction method according to a preferred embodiment of the invention.
Figure 3B:
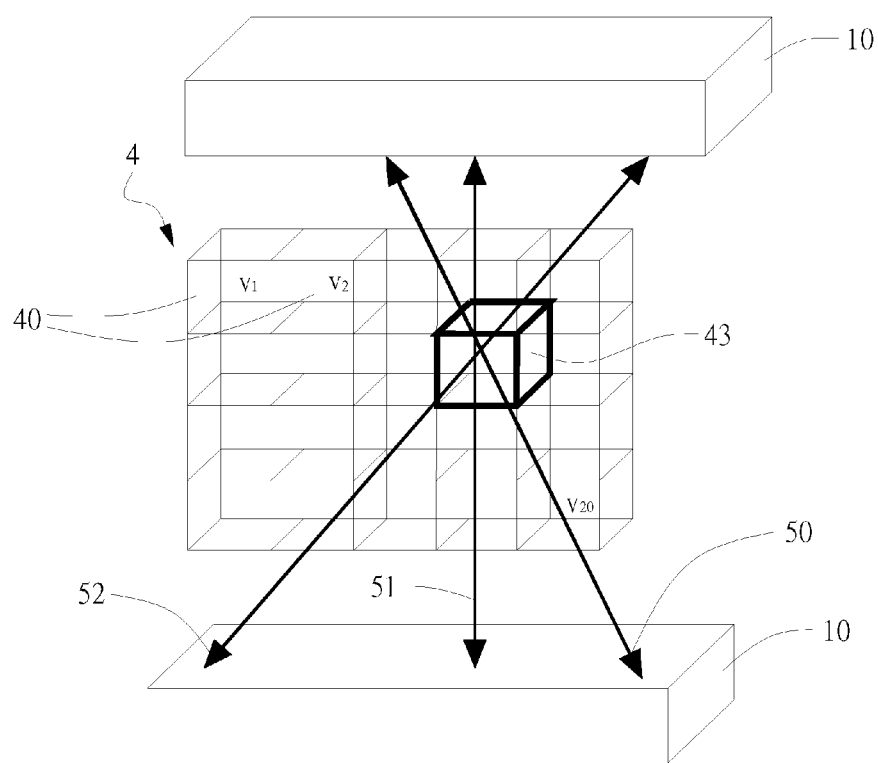
FIG. 3B is a schematic view of an image domain.

For clarity, please refer to FIG. 3B for an schematic diagram of the image domain before proceeding to the next step of the flow shown in FIG. 2. It is noted that the image reconstruction method is designed to be implemented by any imaging system having at least a pair of detectors. In the embodiment shown in FIG. 3B, there are two detectors 10, 11 used in the imaging system, but it is only used for illustration and is not limited thereby. As an object-to-be-imaged is placed between the two detectors 10, 11, an image domain 4 is established therebetween and is being divided into a plurality of voxels 40. In the image domain, each voxel 40 has a first reactivity value, used for representing the intensity of radioactivity inside the voxel.

For simulating a tumor in the object-to-be-imaged, a tracer F-18 fluorodeoxyglucose is injected in the object-to-be-imaged to filled the voxel 43, in which the short-lived radioactive tracer isotope decays by emitting a positron ($\beta^+$), which travels up to a few millimeters and annihilates with an electron, producing a pair of annihilation photons, which is similar to gamma ($\gamma$) rays moving in opposite directions, i.e. being emitted 180° apart. These are detected when they reach a scintillator material in the imaging system coincidentally such that it is referred as an event. For the voxel 43, event can occur with respect to any angle, that is, the pair of gamma rays can be emmited out of the voxel 43 by any angle, and the line of each event is referred as line of response (LOR). There are three LORs 50, 51, 52 used only as representation that there are more LORs than those shown in FIG. 3B.

Please refer to FIG. 3A, which is a block diagram depicting the concept of an image reconstruction method according to a preferred embodiment of the invention. In the present invention, an iterative method is implemented to reconstruct the image by performing projection and back-projection between an image domain 30 and a projection domain 31. During each back-projecting of the image reconstruction, a weighting used in each back-projecting is changed with each iteration. In FIG. 3A, k is the numbering of iteration; $v_i$ represents the $i^{th}$ voxel of the image domain as those 40 shown in FIG. 3B; $f_{v_i}^{(k)}$ represents the first radioactivity value inside the $i^{th}$ voxel after k iteration, whereas the iteration begins with guessing an initial value of the universal constant for all voxel, i.e. the first radioactivity value $f_{v_i}^{(0)}$ can be any constant when k=0; $f_{v_i}^{(k+1)}$ represents the second radioactivity value inside the $i^{th}$ voxel after back-projecting that is used as the first radioactivity value inside the $i^{th}$ voxel for the next iteration; $M_{LOR_j}$ represents an estimated projection value obtained by projecting every voxel passing by the $j^{th}$ LOR into the projection domain; and $\tilde{M}_{LOR_j}$ represents a calibrated value obtained by comparing the estimated projection value of the $j^{th}$ LOR with the measured value of the $j^{th}$ LOR.

Referring back to the flow chart shown in FIG. 2A, after step 20 is accomplished, the flow proceeds to step 21. At step 21, a calibrated value for each LOR can be obtained by performing a projecting upon each LOR while comparing the result of the projection with each measured value of each LOR. Moreover, as shown in FIG. 2B with reference to FIG. 3A and FIG. 3B, the step 21 further comprises step 210, 211 and 212. The flow of FIG. 2B starts at step 210, where an projection value for each LOR can be obtained by projecting the first radioactivity values $f_{v_i}^{(k)}$ of voxels selected form the plural voxels to the projection domain 31 with respect to one of the plural LORs passing the selected voxel; and then the flow proceeds to step 211. At step 211, an estimated projection value $M_{LOR_j}$ of each LOR can be obtained by summing up the projection values of the voxels passing by the same LOR, which is obtained by the formula listed as following:

$$M_{LOR_j} = \int_{LOR_j} f_{v_i}^{(k)} dl_i \quad (1)$$

and then the flow proceeds to step 212. At step 212, a calibrated value $\tilde{M}_{LOR_j}$ for each LOR can be obtained by comparing the estimated projection value $M_{LOR_j}$ to the measured value of each LOR, wherein the $\tilde{M}_{LOR_j}$ can be the ratio of the measured value and the estimated projection value $M_{LOR_j}$.

After step 21 is accomplished, the flow proceeds to step 22. At step 22, the voxels of each LOR in projection domain is back-projecting basing on the relationship between the calibrated value and the first radioactivity value of each voxel of the LOR for converting the same back to the image domain. As seen in FIG. 2C, the step 22 further comprises steps 220 and 221. The flow of FIG. 2C starts at step 220, where a weighting $w_{ij}$ for each voxel can be obtained by performing a calculation upon the first radioactivity value $f_{v_i}^{(k)}$ of each voxel of each LOR with respect to the estimated projection value $M_{LOR_j}$ of its corresponding LOR, and the weighting $w_{ij}$ can be the ratio of the first radioactivity value $f_{v_i}^{(k)}$ and the estimated projection value $M_{LOR_j}$, calculated as the following formula:

$$w_{ij} = f_{v_i}^{(k)} / M_{LOR_j} \quad (2)$$

and then the flow proceeds to step 221. At step 221, b each voxel of each LOR is back-projecting to the image domain 30 basing on the weighting $w_{ij}$ of each voxel After step 22 is accomplished, the flow proceeds to step 23. At step 23, a calculation is performed basing on the relationship between the calibrated value $\tilde{M}_{LOR_j}$ and the first radioactivity value $f_{v_i}^{(k)}$ of each voxel to obtain a second radioactivity value $f_{v_i}^{(k+1)}$ while utilizing the second radioactivity value $f_{v_i}^{(k+1)}$ to update the first radioactivity value $f_{v_i}^{(k)}$ of each voxel of the LOR, and then the flow proceeds to step 24. Moreover, as seen in FIG. 2D, the calculation of step 23 further comprises steps 230, 231 and 232. The flow of FIG. 2D starts at step 230, where a product value is obtained by multiplying each weight of each voxel of each LOR by it corresponding calibrated value, and then the flow proceeds to step 231. At step 231, the second radioactivity value $f_{v_i}^{(k+1)}$ for each voxel of each LOR can be obtained by summing up the product values of the same LOR, whereas the summation is performed by the formula as following:

$$f_{v_i}^{(k+1)} = \Sigma_j \tilde{M}_{LOR_j} w_{ij} \quad (3)$$

and then the flow proceeds to step 232. At step 232, a threshold value δ is defined while setting the second radioactivity value $f_{v_i}^{(k+1)}$ to be zero while the second radioactivity value $f_{v_i}^{(k+1)}$ is smaller than the threshold value δ. By step 231, the speed of image reconstruction can be enhanced as unnecessary operations are avoided. By replacing the previous first radioactivity value $f_{v_i}^{(k)}$ by the obtained second radioactivity value $f_{v_i}^{(k+1)}$, the flow of FIG. 2A is ready for the next iteration. Therefore, as step 22 is accomplished, the flow proceeds to step 23. At step 23, an image reconstruction can be achieve by iterating the step 23 to step 23.

Figure 4:
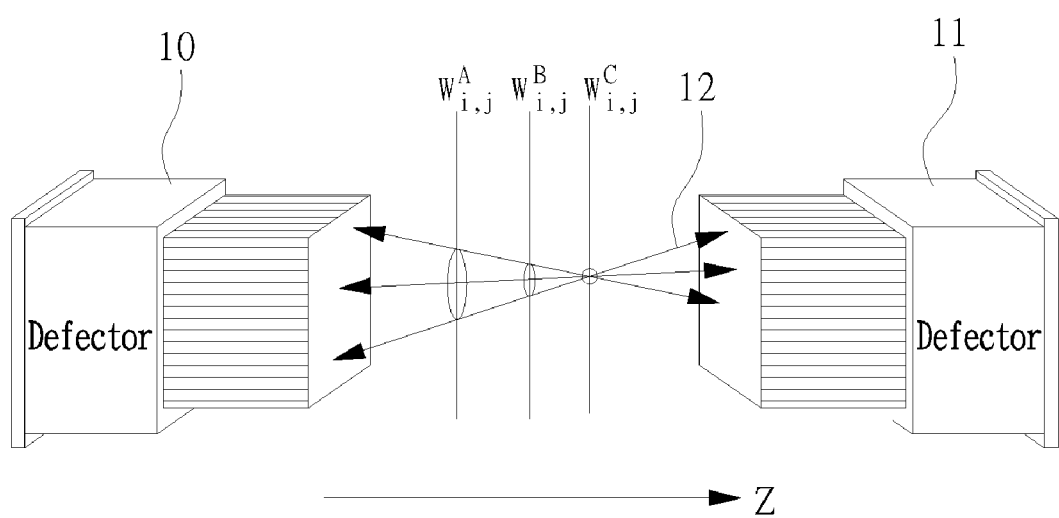
FIG. 4 is a schematic diagram depicting an image reconstruction method according to the present invention.

Please refer to FIG. 4, which is a schematic diagram depicting an image reconstruction method according to the present invention. As seen in FIG. 4, there are three radioactive sources placed between the two detectors 10, 11, whereas the sizes and the location thereof with respect to the Z direction, i.e. positions A, B, and C, are different from each other. Thus, the weightings of the three positions A, B, C, represented by $w_{i,j}^A$, $w_{i,j}^B$, $w_{i,j}^C$, should not be the same. Take the $j^{th}$ LOR shown in FIG. 4 for instance, it is noted that $w_{i,j}^A < w_{i,j}^B < w_{i,j}^C$.

Figure 5:
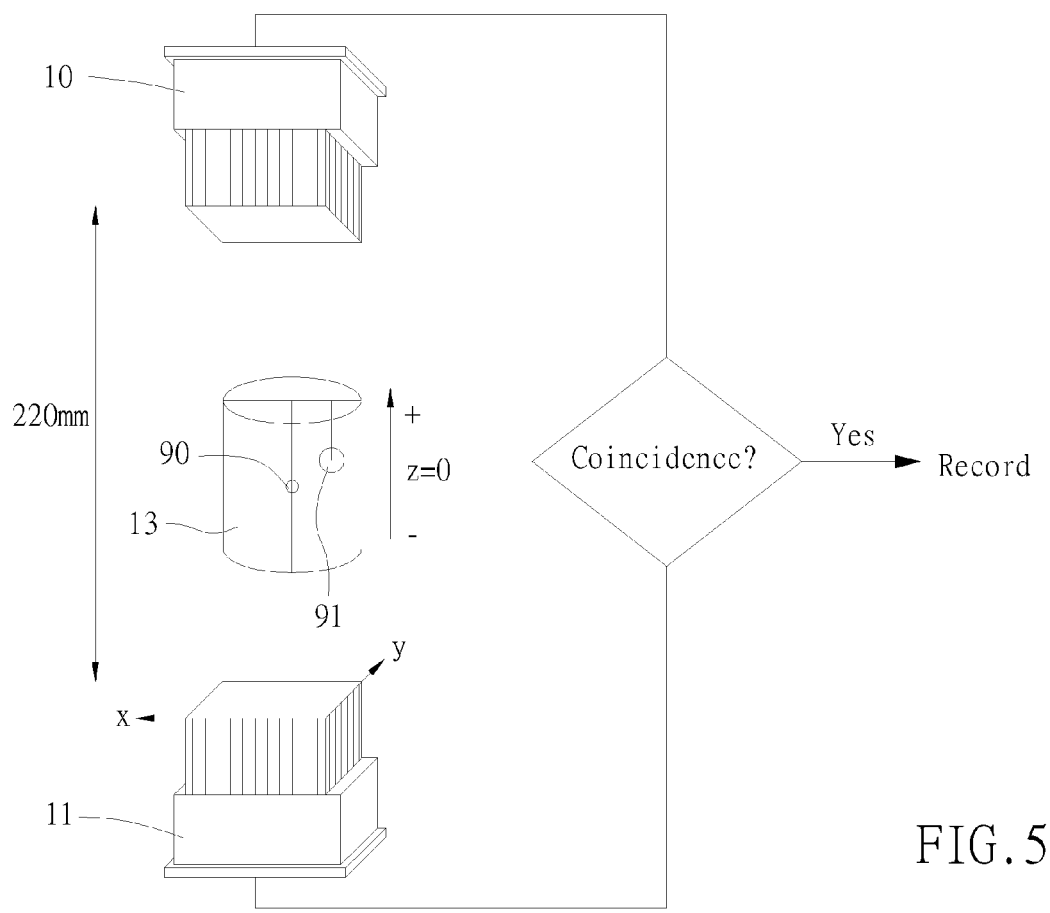
FIG. 5 is a geometric set used for experimenting an image reconstruction method according to the present invention.

Moreover, the image reconstruction method is experimented by the geometric setup shown in FIG. 5. In FIG. 5, projection data is acquired using the two detectors 10, 11 with a detector-to-detector distance of 220 mm as a water-fill cylinder 13 is arranged therebetween, and two radioactive sources 90, 91, used for representing tumors, are arranged in the cylinder 13 at different depth, i.e. at different location with respect to the Z direction. In FIG. 5, the tumor 90 is arranged at the depth of Z=0 while another tumor 91 is arranged at the depth of Z=20 mm. The image reconstruction method of the invention can be implemented by the geometric setup of FIG. 5 so as to compare the resulting image with that reconstructed by conventional focal-plane tomography.

Figure 6:
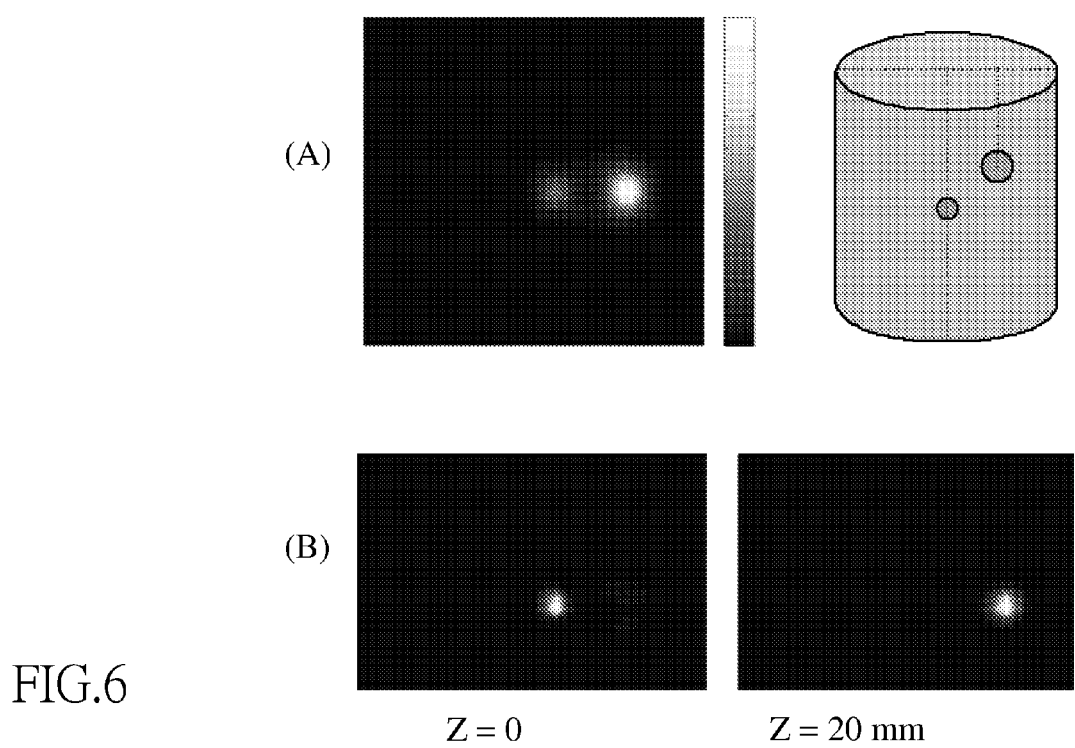
FIG. 6 shows images obtained from conventional focal-plane reconstruction and planar tomography of the invention, whereas a water-fill cylinder having two hollow spheres filled with radioactive solutions are scanned thereby as the two radiation spheres are respectively being placed at Z=0 mm and Z=20 mm.

Please refer to FIG. 6, which shows images obtained from conventional focal-plane reconstruction and planar tomography of the invention, whereas a water-fill cylinder having two hollow spheres filled with radioactive solutions are scanned thereby as the two radiation spheres are respectively being placed at Z=0 mm and Z=20 mm. The picture (A) of FIG. 6 is obtained from conventional focal-plane reconstruction, and the pictures (B) of FIG. 6 are obtained form the image reconstruction method of the invention. From those pictures (A), (B) shown in FIG. 6, it is clear that the images of the present invention are able to identify the depths of the tumors, i.e. the locations with respect to the Z direction while that of the conventional focal-place reconstruction can not.

Figure 7:
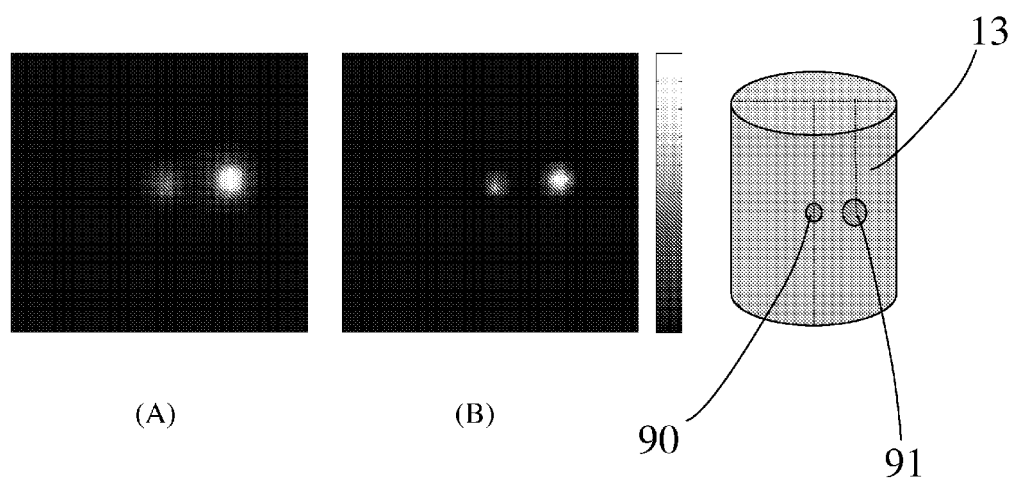
FIG. 7 shows images obtained from conventional focal-plane reconstruction and planar tomography of the invention, whereas a water-fill cylinder having two hollow spheres filled with radioactive solution are scanned thereby as the two radiation spheres are placed at the positions of the same depth.

Please refer to FIG. 7, which shows images obtained from conventional focal-plane reconstruction and planar tomography of the invention, whereas a water-fill cylinder 13 having two hollow spheres 90, 91 filled with radioactive solution are scanned thereby as the two radiation spheres are placed at the positions of the same depth. The picture (A) of FIG. 7 is obtained from conventional focal-plane reconstruction, and the picture (B) of FIG. 7 is obtained form the image reconstruction method of the invention. From those pictures (A), (B) shown in FIG. 6, it is clear that the image of the present invention is superior in contrast and size identification that those shown in image of conventional method.

Figure 8:
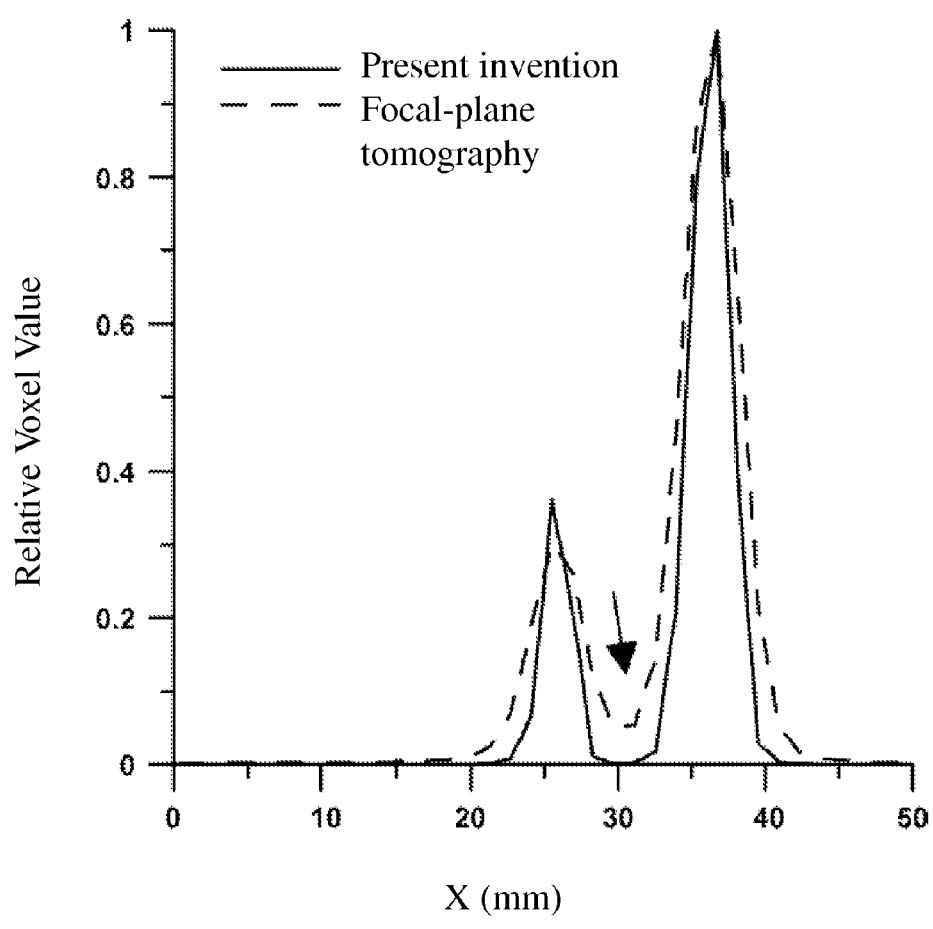
FIG. 8 shows profiles obtained from the images reconstructed by focal-plane and planar tomography of the invention.

FIG. 8 shows the profiles of two radioactive spheres plotted respectively by data obtained from the planar tomography of the present invention and the focal-place tomography, where as the planar tomography of the present invention is represented by the profile of solid line and the focal-place tomography is represented by the profile of dotted line. It reveals that the planar tomography of the present invention better estimates the background radioactivity between the two radioactive spheres, indicating that the planar tomography has better contrast performance than the focal-plane reconstruction. The comparison of planar tomography and focal-plane reconstruction shows that the planar tomography performs better in determining the Z-direction locations of tumors and improves the image quality, regardless of whether the tumors were located at different, or the same Z depths.

The scanner implementing the image reconstruction method of the invention will has fewer detectors than regular whole-ring PET scanners, so that not only cost is lower, but also it can be a compact device and thus is preferred comparing to the bulky and expensive whole-ring PET scanners.

From the above description, it is noted that, by the image reconstruction method of the invention, not only the detection sensitivity is increased, but also the image quality can be enhanced so that it has the potential to detect early cancers simply, effectively, and inexpensively.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. An image reconstruction method for structuring planar images into three-dimension images, being adopted to perform an image reconstruction operation with respect to a plurality of measured values, respectively corresponding to a plurality of lines of response (LOR) obtained from the detecting of an object-to-be-imaged, comprising steps of:
   (a) utilizing a plurality of voxels, each having a first radioactivity value, to construct an image domain with reference to the object-to-be-imaged;
   (b) projecting the plural voxels with respect to each LOR in respective for converting the same to a projection domain while comparing the result of the projection respectively with the measured values to obtain a plurality of calibrated values corresponding to the plural LORs in respective;
   (c) obtaining a weighting for each voxel based on an operation performed upon the first radioactivity value of each voxel with respect to a corresponding LOR, wherein the weighting of a voxel with respect to a LOR is the ratio of the first radioactivity value of the voxel and the totality of the first radioactivity value of all voxels passing by the LOR;
   (d) performing a back-projection operation basing on the weighting of each voxel of each LOR so as to perform a calculation upon the calibrated values of each LOR with respect to the weightings for obtaining a second radioactivity value for each voxel of each LOR;
   (e) converting the second radioactivity value of each voxel into an updated first radioactivity value by projecting the same back to the image domain; and
   (f) repeating the step (b) to step (f) by an iterative manner.

2. The image reconstruction method of claim 1, wherein the step (d) further comprises a step of:
   (d1) defining a threshold value and setting the second radioactivity value to be zero while the second radioactivity value is smaller than the threshold value.

3. The image reconstruction method of claim 1, wherein the step (b) further comprises steps of:
   (b1) projecting the first radioactivity values of voxels selected form the plural voxels to a projection domain with respect to one of the plural LORs passing the selected voxel so as to correspondingly obtain an estimated projection value for each LOR; and
   (b2) comparing the estimated projection value to the measured value of each LOR so as to obtain a calibrated value for each LOR. It is noted that the calibrated value can be the ratio of the measured value and the estimated projection value.

4. The image reconstruction method of claim 3, wherein the calibrated value is the ratio of the measured value and the estimated projection value.

5. The image reconstruction method of claim 1, wherein the calculation of step (d) further comprises steps of:
   (d2) obtaining a product value by multiplying each weight of each voxel of each LOR by it corresponding calibrated value; and
   (d3) summing up the product values of the same LOR to obtain the second radioactivity value for each voxel of each LOR.

6. The image reconstruction method of claim 5, wherein the calculation of step (d) further comprises steps of:
   (d4) defining a threshold value and setting the second radioactivity value to be zero while the second radioactivity value is smaller than the threshold value.

* * * * *